United States Patent
Nawrocki et al.

(10) Patent No.: US 10,973,513 B2
(45) Date of Patent: *Apr. 13, 2021

(54) BARBED SUTURE HAVING INCREASED HOLDING STRENGTH

(75) Inventors: Jesse G. Nawrocki, Annandale, NJ (US); David C. Lindh, Sr., Flemington, NJ (US); Jason T. Perkins, Easton, PA (US); Dennis L. Furman, East Windsor, NJ (US)

(73) Assignee: ETHICON, LLC, San Lorenzo, PR (US)

(*) Notice: Subject to any disclaimer, the term of this patent is extended or adjusted under 35 U.S.C. 154(b) by 0 days.

This patent is subject to a terminal disclaimer.

(21) Appl. No.: 13/248,542

(22) Filed: Sep. 29, 2011

(65) Prior Publication Data

US 2013/0085525 A1 Apr. 4, 2013

(51) Int. Cl.
| | | |
|---|---|---|
| *A61B 17/04* | (2006.01) | |
| *A61B 17/06* | (2006.01) | |
| *A61B 17/00* | (2006.01) | |

(52) U.S. Cl.
CPC .... *A61B 17/06166* (2013.01); *A61B 17/0401* (2013.01); *A61B 2017/00004* (2013.01); *A61B 2017/0417* (2013.01); *A61B 2017/0464* (2013.01); *A61B 2017/06176* (2013.01)

(58) Field of Classification Search
CPC .... A61B 17/06166; A61B 2017/00004; A61B 2017/06176; A61B 2017/0464; A61B 2017/0417; A61B 17/0401
USPC ........ 606/228, 224, 222, 223, 144, 232, 300
See application file for complete search history.

(56) References Cited

U.S. PATENT DOCUMENTS

| | | | |
|---|---|---|---|
| 5,053,047 A | | 10/1991 | Yoon |
| 5,123,913 A | * | 6/1992 | Wilk et al. ................. 606/232 |
| 5,222,976 A | | 6/1993 | Yoon |
| 5,312,436 A | * | 5/1994 | Coffey ............... A61B 17/0469 |
| | | | 606/224 |
| 5,403,346 A | | 4/1995 | Loeser |
| 5,450,860 A | * | 9/1995 | O'Connor .................... 128/898 |
| 5,683,417 A | | 11/1997 | Cooper |
| 5,697,950 A | | 12/1997 | Fucci et al. |
| 5,707,394 A | | 1/1998 | Miller et al. |
| 6,033,430 A | | 3/2000 | Bonutti |

(Continued)

FOREIGN PATENT DOCUMENTS

| | | |
|---|---|---|
| CN | 1830200 | 5/2010 |
| EP | 1867288 B1 | 12/2007 |

(Continued)

OTHER PUBLICATIONS

International Search Report for International Application No. PCT/US2012/056858 dated Nov. 29, 2012.

*Primary Examiner* — Diane D Yabut

(57) ABSTRACT

A wound closure device having a filamentary element having a proximal end and a distal end, and a stop element coupled thereto and having a leading edge area defined by thickness and a width and having a total surface area. The leading edge area is substantially perpendicular to a longitudinal axis of the filamentary element. The device may have a ratio of the leading edge area to the total surface area that is less than 10%, a ratio of the length to the maximum thickness of the stop element that is at least 4, or a ratio of the length to the width of the stop element is at least 1 for any given thickness.

21 Claims, 4 Drawing Sheets

(56) References Cited

U.S. PATENT DOCUMENTS

| | | | |
|---|---|---|---|
| 6,050,998 A * | 4/2000 | Fletcher | A61B 17/688 606/103 |
| 6,117,139 A | 9/2000 | Shino | |
| RE36,974 E | 11/2000 | Bonutti | |
| 6,241,747 B1 | 6/2001 | Ruff | |
| 6,264,675 B1 | 7/2001 | Brotz | |
| 6,319,263 B1 | 11/2001 | Levinson | |
| 6,730,112 B2 | 5/2004 | Levinson | |
| 7,468,068 B2 | 12/2008 | Kolster | |
| 7,731,732 B2 | 6/2010 | Ken | |
| 7,850,700 B2 | 12/2010 | Sakura | |
| 7,850,894 B2 | 12/2010 | Lindh, Sr. et al. | |
| 8,142,513 B2 | 3/2012 | Shalon et al. | |
| 8,267,961 B2 | 9/2012 | Popadiuk et al. | |
| 8,715,320 B2 | 5/2014 | Lindh, Sr. | |
| 8,721,681 B2 | 5/2014 | Ruff et al. | |
| 2001/0044639 A1 * | 11/2001 | Levinson | 606/228 |
| 2003/0149447 A1 | 8/2003 | Morency et al. | |
| 2004/0122456 A1 | 6/2004 | Saadat et al. | |
| 2005/0004576 A1 | 1/2005 | Benderev | |
| 2005/0049635 A1 * | 3/2005 | Leiboff | 606/213 |
| 2007/0257395 A1 * | 11/2007 | Lindh et al. | 264/171.12 |
| 2008/0200751 A1 * | 8/2008 | Browning | 600/30 |
| 2008/0281357 A1 | 11/2008 | Sung et al. | |
| 2008/0312688 A1 | 12/2008 | Nawrocki et al. | |
| 2009/0018577 A1 | 1/2009 | Leung et al. | |
| 2009/0076547 A1 | 3/2009 | Sugimoto et al. | |
| 2009/0248067 A1 | 10/2009 | Maiorino | |
| 2009/0248070 A1 | 10/2009 | Kosa et al. | |
| 2009/0312791 A1 | 12/2009 | Lindh, Sr. et al. | |
| 2010/0084780 A1 | 4/2010 | Lindh, Sr. et al. | |
| 2010/0146770 A1 | 6/2010 | Morency et al. | |
| 2010/0211098 A1 | 8/2010 | Hadba et al. | |
| 2010/0274283 A1 * | 10/2010 | Kirsch | A61B 17/0401 606/228 |
| 2010/0298871 A1 | 11/2010 | Ruff et al. | |
| 2011/0054522 A1 | 3/2011 | Lindh, Sr. et al. | |
| 2011/0093010 A1 | 4/2011 | Genova et al. | |
| 2011/0106152 A1 | 5/2011 | Kozlowski | |
| 2012/0016183 A1 | 1/2012 | Gellman | |
| 2012/0046525 A1 | 2/2012 | Russell et al. | |
| 2013/0085525 A1 | 4/2013 | Nawrocki et al. | |

FOREIGN PATENT DOCUMENTS

| | | |
|---|---|---|
| EP | 1857236 B1 | 11/2009 |
| EP | 1858243 B1 | 11/2009 |
| GB | 1091282 A | 11/1967 |
| JP | 2010-184109 | 8/2010 |
| RU | 2400162 C2 | 9/2010 |
| WO | 9506447 A1 | 3/1995 |
| WO | 2004030704 | 4/2004 |
| WO | WO 2009/020795 A1 | 2/2009 |
| WO | WO 2010/051506 A1 | 5/2010 |
| WO | 2013048947 | 4/2013 |
| WO | WO 2013/048947 A1 | 4/2013 |
| WO | 2019060365 A1 | 3/2019 |

* cited by examiner

BARBED SUTURE HAVING INCREASED HOLDING STRENGTH

FIELD OF THE INVENTION

The present invention relates generally to the field of medical devices, and more particularly to barbed suture devices having increased holding strength.

BACKGROUND

Many wound and surgical incisions are closed using surgical sutures or some other surgical closure device. Barbed sutures are well known and have recently been gaining attention for various medical applications. Typically, barbed sutures are constructed with a series of "barbs" or "protrusions" (used interchangeably herein) that extend outwardly from the suture, and function to increase the holding strength of the suture and/or eliminate the need for knot tying. The size and shape of the barbs have practical limitations in a surgical setting, and cannot simply be increased wherever increased holding strength is desired.

Some sutures and barbed sutures have been known to include anchors, tabs or the like on the distal end of the suture to provide a "stop" at the end that increases the holding strength of the suture and eliminates the need to tie knots to secure the suture. Conventional thinking dictates that the larger the surface area of the stop in a direction perpendicular to the direction of insertion of the suture, the more holding strength that will be achieved. Again, there are practical limitations on size however, as large masses may be intolerable in surgical procedures and/or palpable and therefore undesirable. Further, with T-shaped stops, the perpendicular portion is structurally weak when a bending moment is applied as it would be when pulling on the suture to approximate a wound.

Therefore, there remains a need to enhance the holding strength of a surgical suture without significantly increasing the insertion force, stiffness of the suture, or palpability of the device.

SUMMARY OF THE INVENTION

The present invention provides a wound closure device including a filamentary element having a proximal end and a distal end, a stop element coupled to the distal end of the filamentary element and having a leading edge area defined by thickness and a width, and a total surface area. The leading edge area faces substantially perpendicular to a longitudinal axis of the filamentary element, and the ratio of the leading edge area to the total surface area is less than 10%. According to one embodiment, the ratio is less than 5%.

According to various embodiments, the width of the stop element may be greater than 70 mils, the length of the stop element may be greater than 70 mils, and/or the maximum thickness of said stop element may be between 6 and 25 mils.

According to one embodiment, the thickness of the stop element varies, and/or a minimum thickness of the stop element may be between 4 and 12 mils. According to yet another embodiment, the leading edge thickness includes a maximum thickness at a center and/or at first and/or second outer edges, and a minimum thickness at a location between the center and the first outer edge and between the center and the second outer edge.

In yet another embodiment, the wound closure device further includes a plurality of projections extending outwardly from the filamentary element along at least a portion of its length. The plurality of projections may extend outwardly from said filamentary element by approximately 6-25 mils.

The device may be made of a polymeric, metallic or ceramic material that are absorbable or non-absorbable. In yet another embodiment, the device is made of a polymer material selected from the group consisting of absorbable and non-absorbable homopolymers, random copolymers, block copolymers or blends made from polydioxanone, polyglactin, polyglycolic acid, copolymers of glycolide, lactide, and/or caprolactone, polyoxaesters, poliglecaprone, polypropylene, polyethylene, polyvinylidene fluoride (PVDF), hexafluoropropylene, copolymers of vinylidene fluoride and hexafluoropropylene, polyesters, polyethylene terephthalate, polybutylene terephthalate, glycol-modified polyethylene terephthalate, polytetrafluoroethylene, fluoropolymers, thermoplastic elastomers, ionomers, copolymers of ethylene and methacrylic acid, polyamides, polytetramethylene oxide, polystyrene, polybutadiene, polybutylene, etc. including combinations and/or copolymers of absorbable and non-absorbable materials.

According to yet another embodiment, a ratio of the length to maximum thickness of the stop element is greater than 4.

In yet another embodiment, the maximum thickness of the stop is approximately 8-25 mils, the width of the stop is approximately 70-120 mils, and the length of the stop is approximately 39-200 mils.

The present invention also provides a wound closure device including a filamentary element extending along a longitudinal axis between a proximal end and a distal end, and a stop element coupled to the distal end of the filamentary element and that has a length extending substantially parallel to the longitudinal axis of the filamentary element, a width extending substantially perpendicular to said longitudinal axis, and a maximum thickness. The ratio of the length to the maximum thickness of the stop element is at least 4.

In alternate embodiments, the maximum thickness of the stop element is between 8 and 25 mils, the length of the stop element is greater than 39 mils, and/or the width of the stop element is between 70 and 120 mils.

In yet another embodiment, the wound closure device further includes a plurality of projections extending outwardly from the filamentary element along at least a portion of its length.

In yet another embodiment, the thickness of the stop element varies, and in another particular embodiment, the leading edge thickness includes a maximum thickness at a center and/or at first and/or second outer edges, and a minimum thickness at a location between the center and the first outer edge and between the center and the second outer edge.

Also provided is a wound closure device including a filamentary element extending along a longitudinal axis between a proximal end and a distal end, and a stop element coupled to the distal end of the filamentary element. The stop element has a length extending substantially parallel to the longitudinal axis of the filamentary element, a width extending substantially perpendicular to said longitudinal axis, and a maximum thickness, and for any given maximum thickness of the stop element, the ratio of the length to the width of the stop element is at least 1.

In a further embodiment, the ratio of the length to the width of the stop element is at least 1.5.

These and other objects, features and advantages of the present invention will be apparent from the following detailed description of illustrative embodiments thereof, which is to be read in connection with the accompanying drawings.

DETAILED DESCRIPTION

Figure 1:
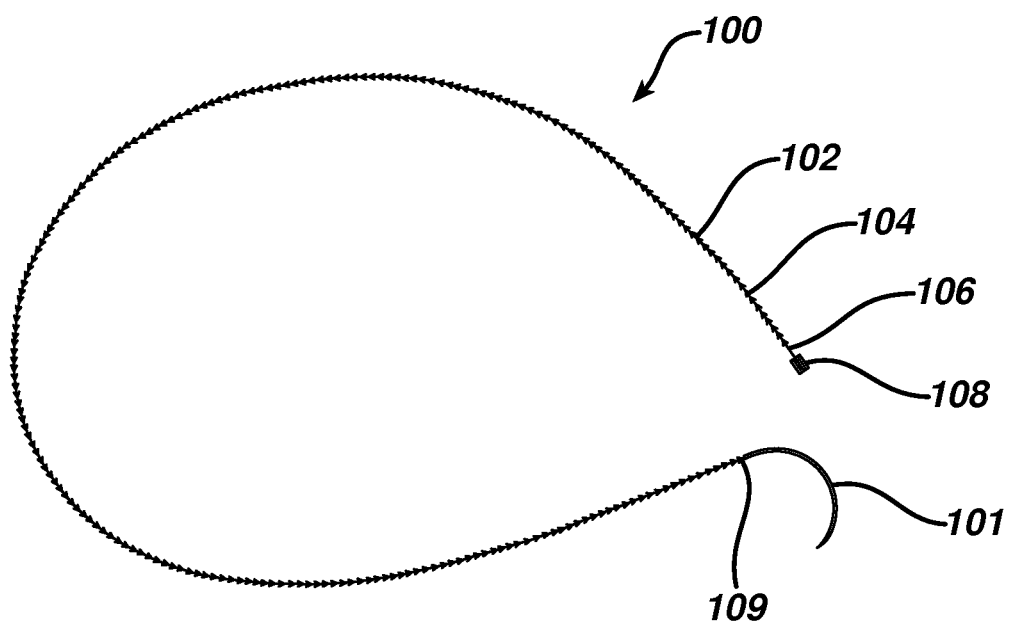
FIG. 1 illustrates a wound closure device according to the present invention including an insertion needle.
Figure 2:
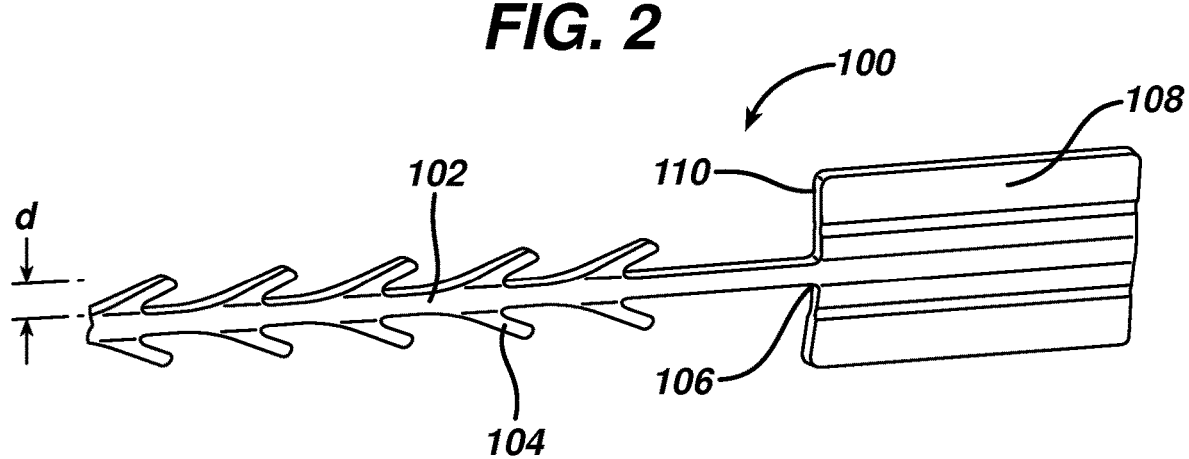
FIG. 2 is an enlarged view of the distal end of the wound closure device of FIG. 1.
Figure 3:
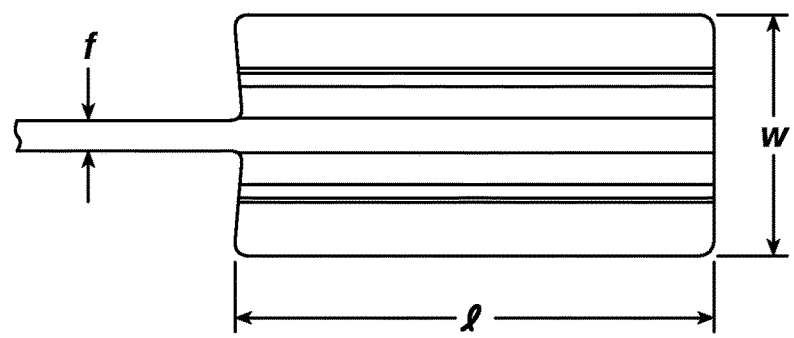
FIG. 3 is a top view of the stop element of the wound closure device of FIG. 1.
Figure 4:
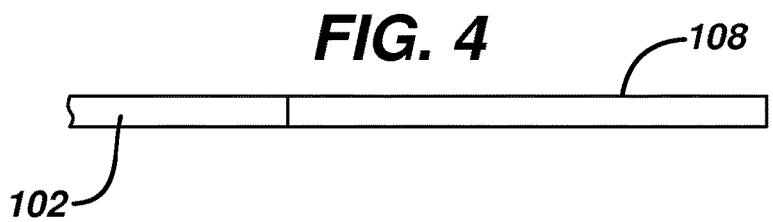
FIG. 4 is a side view of the stop element of the wound closure device of FIG. 1.
Figure 5:
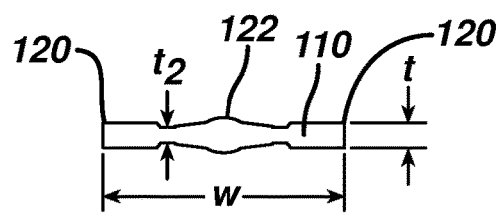
FIG. 5 is a cross-sectional view of the leading edge of the stop element of the wound closure device of FIG. 1.
Figure 6:
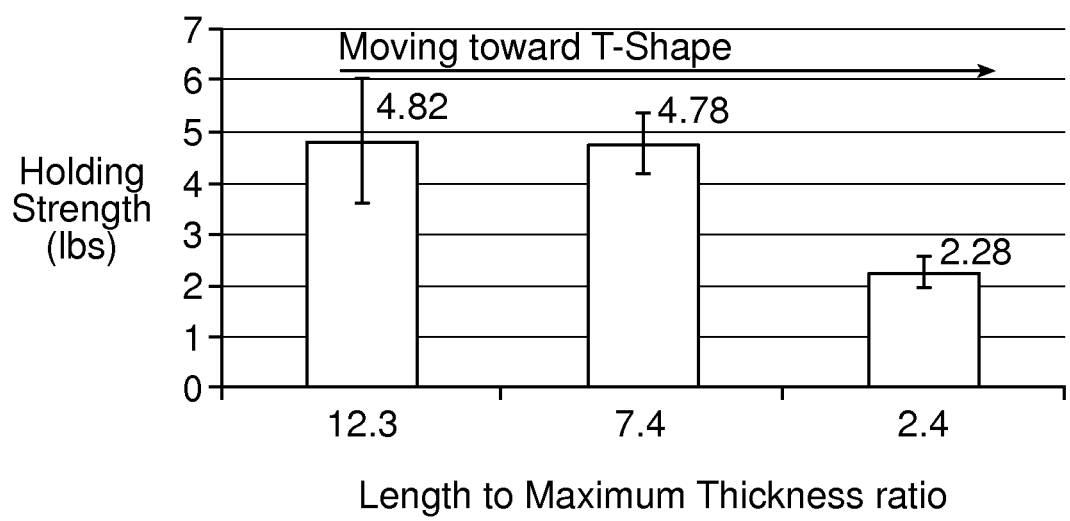
FIG. 6 is a graph illustrating the holding strength of fixation tabs of equal leading edge maximum thickness and width, but with varying length.

FIG. 1 illustrates an exemplary embodiment of a wound closure device 100 according to the present invention. The wound closure device 100 includes a filamentary element 102 comprised of any suitable surgical suture material (i.e., absorbable and non-absorbable polymeric materials, metallic, or ceramic materials) that preferably includes a plurality of barbs 104 that extend outwardly therefrom. The suture may be formed by any suitable method, but preferably is compound profile punched from preformed material in a manner described in more detail in U.S. Patent Publication No. 2007/0257395, which is incorporated herein by reference in its entirety. The proximal end 109 of the wound closure device may include a needle or other insertion device 101. At the distal end 106 of the wound closure device is a fixation tab or stop element or the like 108. The stop 108 has a leading edge 110 defined by a leading edge thickness t and a leading edge width w, and also has a length l as shown in FIGS. 3-5. As indicated previously, known T-shaped configurations have relatively weak stiffness when a bending moment is applied, such as when tension is applied to the suture to approximate a wound. The graph depicted in FIG. 6 more clearly illustrates the advantage of the present invention over a T-shaped end configuration. Fixation tabs of equal leading edge maximum thickness (t) and width (w) (leading edge area), but varying length (l) were made and the holding strength tested. The holding strength was tested by passing the barbed suture through a porcine abdominal wall fascia sample and pulling against the fixation tab until failure occurred either by the stop breaking in some fashion, the stop pulling through the tissue, or a combination of both. The maximum load prior to failure was recorded and illustrated in FIG. 6.

As shown therein, the holding strength decreases as the geometry becomes more like a T-shaped member, or in other words, as the ratio of length to leading edge area or length to maximum thickness decreases. The holding strength can be increased by increasing the thickness or width of the stop, but as indicated previously, there are practical and clinical limitations on the size and mass that can be implanted.

Figure 7:
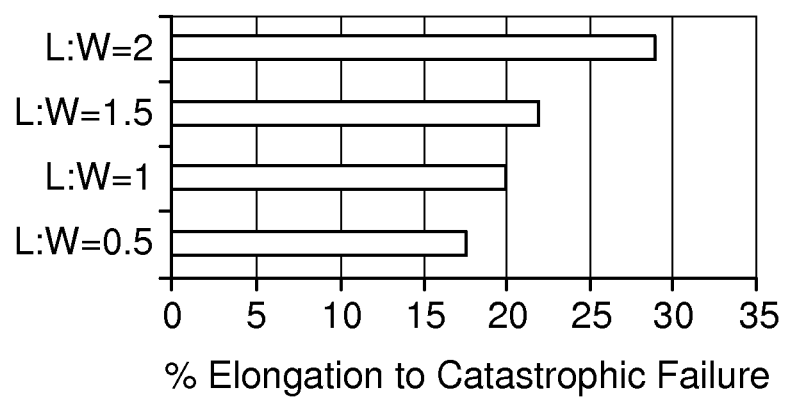
FIG. 7 is a graph illustrating elongation of a fixation tab as a function of length to width ratio for a given maximum thickness.

In addition to the length to maximum thickness or leading edge area ratio, the length l to width w ratio is also a significant consideration for any given maximum thickness. Surprisingly and counter-intuitively, a ratio of at least 1:1 provides much increased holding strength. FIG. 7 illustrates the elongation of the fixation stop or tab as a function of the length to width ratio for a given maximum thickness. As shown, the percentage of elongation (or more simply the amount of deformation) required to reach catastrophic failure increases with increasing length to width ratio.

Figure 8:
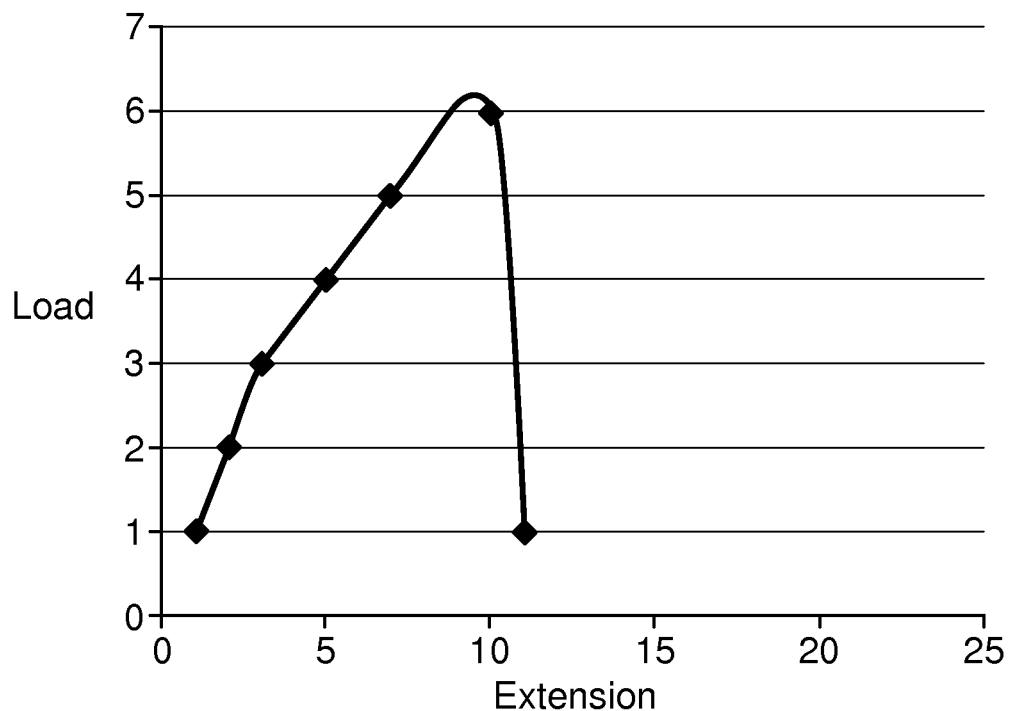
FIG. 8 is a graph illustrating a load-extension curve for a fixation tab length to width ratio of 0.5.
Figure 9:
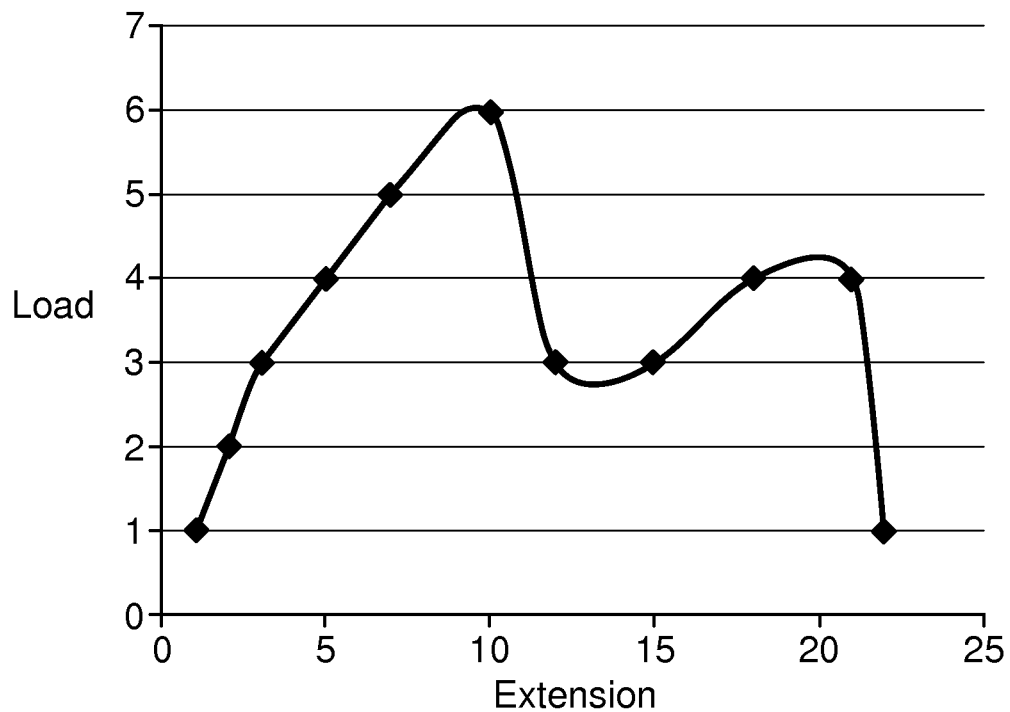
FIG. 9 is a graph illustrating a load-extension curve for a fixation tab length to width ratio of 2.

In addition to raw elongation percentages, the actual amount of energy required for the failure of the device increases with increasing length to width ratios. This is illustrated by FIGS. 8 and 9, in which the area under the load-extension curve is a measure of the strain energy until catastrophic failure. As the length to width ratio increases, the amount of strain energy required to reach catastrophic failure significantly increases. FIG. 8 illustrates a load-extension curve for a fixation tab having a length to width ratio of 0.5:1. As illustrated, the device reaches a peak load then decreases dramatically with sudden failure. FIG. 9 illustrates a load-extension curve for a fixation tab having a length to width ratio of 2:1. As illustrated, the curve has a second peak, and much greater extension before catastrophic failure occurs. In other words, the strain energy significantly increases as the length to width ratio increases from 0.5 to 2.

Referring once again to FIGS. 3-5, the leading edge area of the stop element has relatively little surface area in contact with tissue when the suture is under tension, but its ratio of length l to maximum thickness t is very large. Thus, the actual area in contact with tissue (leading edge area 110) in the direction of load is very small relative to the overall dimensions of the fixation stop or tab. This relatively long length, but minimal thickness allows the stop to be placed in the wound in a relatively flat position, which minimizes palpability and allows the opposing sides of the tissue to neatly cover the stop. Since the stop lies nicely in the tissue, it can be placed at the apex of the wound, lateral to one side of the wound etc, without impeding the surgeon's individual closure technique.

In a preferred embodiment, the leading edge relative to the total surface area of the stop (sum of surface area of all sides) is small, preferably less than 10% and more preferably less than 5%. This is counterintuitive, as conventional thinking dictates that in order to increase holding strength and/or minimize failure, one must increase or maximize the surface area under load in order to spread out the load and decrease the load per unit area. The relatively long length l, but minimal thickness t results in clinical advantages, including flat positioning that minimizes palpability, and versatile positioning as mentioned above.

According to a preferred embodiment shown in detail in the cross-sectional view of FIG. 5, the leading edge area of the stop of the present invention preferably is not rectangular, but rather has a thickness that varies across its width. The preferred stop 108 has a maximum thickness t at its outer edges 120 and center 122, and a minimum thickness $t_2$ at points between the center and outer edges. In this embodiment, the filamentary element has a filament width f of approximately 5-25 mils, and the barbs 104 extend outwardly therefrom by a distance d of approximately 6-25 mils. The stop has a length l of at least 39 mils, preferably 100 to 200 mils, and a width of greater than 70 mils, more preferably greater than 90 mils, and most preferably greater than 95 mils. Further, the maximum thickness t is greater than 6 mils, and preferably between 10 and 25 mils, and the minimum thickness $t_2$ is less than 15 mils, but preferably between approximately 5 and 9 mils. The length to maximum thickness ratio is preferably greater than 4, and the length to minimum thickness is preferably greater than 9. Finally, the length to width ratio is greater than 1, and preferably greater than 1.5.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A surgical suture adapted to approximate opposing tissue surfaces without knot tying, the surgical suture having a first end and a second end comprising:
   a filamentary element having a proximal end and a distal end, a plurality of barbs extending outwardly therefrom so as to allow movement of the surgical suture through tissue in a first direction toward the proximal end of the filamentary element and first end of the surgical suture and resist movement in a second opposite direction;
   a stop element having a total surface area and a substantially planar leading edge area defined by thickness and a width, wherein the stop element is coupled to the distal end of the filamentary element so that the leading edge area is substantially perpendicular to a longitudinal axis of the filamentary element and faces the first end of the surgical suture and lies substantially within a first plane, the stop element also having a length extending in the direction of the longitudinal axis of the filamentary element that is greater than the width, the stop element adapted to resist movement of the surgical suture in said first direction;
   wherein a ratio of the leading edge area to the total surface area is less than 10%,
   and wherein the filamentary element and stop element are comprised of the same polymeric material.

2. The surgical suture according to claim 1, wherein the ratio of the leading edge area to the total surface area is less than 5%.

3. The surgical suture according to claim 1, wherein the width of the stop element is greater than 70 mils.

4. The surgical suture according to claim 3, wherein a length of the stop element is greater than 70 mils.

5. The surgical suture according to claim 1, wherein a maximum thickness of said stop element is between 6 and 25 mils.

6. The surgical suture according to claim 1, wherein the thickness of the stop element varies.

7. The surgical suture according to claim 6, wherein a minimum thickness of the stop element is between 4 and 12 mils.

8. The surgical suture according to claim 6, wherein the leading edge thickness includes a maximum thickness at a center and/or at first and/or second outer edges, and a minimum thickness at a location between the center and the first outer edge and between the center and the second outer edge.

9. The surgical suture according to claim 1, further comprising a plurality of projections extending outwardly from the filamentary element along at least a portion of its length.

10. The surgical suture according to claim 9, wherein said plurality of projections extending outwardly from said filamentary element by approximately 6-25 mils.

11. The surgical suture according to claim 1, wherein the polymeric is absorbable or non-absorbable.

12. The surgical suture according to claim 11, wherein the polymeric material selected from the group consisting of absorbable and non-absorbable homopolymers, random copolymers, block copolymers or blends made from polydioxanone, polyglactin, polyglycolic acid, copolymers of glycolide, lactide, and/or caprolactone, polyoxaesters, poliglecaprone, polypropylene, polyethylene, polyvinylidene fluoride (PVDF), hexafluoropropylene, copolymers of vinylidene fluoride and hexafluoropropylene, polyesters, polyethylene terephthalate, polybutylene terephthalate, glycol-modified polyethylene terephthalate, polytetrafluoroethylene, fluoropolymers, thermoplastic elastomers, ionomers, copolymers of ethylene and methacrylic acid, polyamides, polytetramethylene oxide, polystyrene, polybutadiene, polybutylene, etc. including combinations and/or copolymers of absorbable and non-absorbable materials.

13. The surgical suture according to claim 1, wherein a ratio of a length to maximum thickness of the stop element is greater than 4.

14. The surgical suture according to claim 1, wherein a maximum thickness of the stop is approximately 8-25 mils, the width of the stop element is approximately 70-120 mils, and a length of the stop element is approximately 39-200 mils.

15. A surgical suture adapted to approximate opposing tissue surfaces without knot tying comprising:
   a filamentary element extending along a longitudinal axis between a proximal end and a distal end, and having a plurality of barbs extending outwardly therefrom so as to allow movement of the surgical suture through tissue in a first direction toward the proximal end of the filamentary element and resist movement in a second opposite direction;
   a stop element having a length extending substantially parallel to the longitudinal axis of the filamentary element, and having a substantially planar leading edge area extending substantially perpendicular to said longitudinal axis and defined by a width and a maximum thickness, the leading edge area being fixedly coupled to the distal end of the filamentary element along said leading edge area;
   wherein the ratio of the length to the maximum thickness of the stop element is at least 4.

16. The surgical suture according to claim 15, wherein the maximum thickness of the stop element is between 8 and 25 mils.

17. The surgical suture according to claim 16, wherein the length of the stop element is greater than 39 mils.

18. The surgical suture according to claim 17, wherein the width of the stop element is between 70 and 120 mils.

19. The surgical suture according to claim 17, further comprising a plurality of projections extending outwardly from the filamentary element along at least a portion of its length.

20. The surgical suture according to claim 17, wherein a thickness of the stop element varies.

21. The surgical suture according to claim 20, wherein a leading edge of the stop element includes a maximum thickness at a center and/or at first and/or second outer edges, and a minimum thickness at a location between the center and the first outer edge and between the center and the second outer edge.

* * * * *